United States Patent [19]
Geddes et al.

[11] Patent Number: 5,690,681
[45] Date of Patent: Nov. 25, 1997

[54] METHOD AND APPARATUS USING VAGAL STIMULATION FOR CONTROL OF VENTRICULAR RATE DURING ATRIAL FIBRILLATION

[75] Inventors: Leslie A. Geddes, West Lafayette, Ind.; Tarek Elabbady, Kirkland, Wash.; William E. Schoenlein, Lafayette, Ind.; Matthew Waninger, Frankfort; Joe D. Bourland, West Lafayette, both of Ind.

[73] Assignee: Purdue Research Foundation, West Lafayette, Ind.

[21] Appl. No.: 624,109

[22] Filed: Mar. 29, 1996

[51] Int. Cl.$^6$ ............................................. A61N 1/00
[52] U.S. Cl. ..................................................... 607/2
[58] Field of Search ......................... 607/4, 5, 9, 2, 607/44; 128/702, 703, 705

[56] References Cited

U.S. PATENT DOCUMENTS

| | | |
|---|---|---|
| 3,650,277 | 3/1972 | Sjostrand et al. . |
| 3,796,221 | 3/1974 | Hagfors . |
| 3,850,161 | 11/1974 | Liss . |
| 3,918,461 | 11/1975 | Cooper . |
| 4,280,502 | 7/1981 | Baker et al. . |
| 4,573,481 | 3/1986 | Bullara . |
| 4,867,164 | 9/1989 | Zabara . |
| 4,890,617 | 1/1990 | Markowitz et al. . |
| 4,998,974 | 3/1991 | Aker . |
| 5,086,772 | 2/1992 | Larnard et al. . |
| 5,107,850 | 4/1992 | Olive ................................. 128/705 |
| 5,144,947 | 9/1992 | Wilson . |

(List continued on next page.)

FOREIGN PATENT DOCUMENTS

| | | |
|---|---|---|
| 0 688 577 A1 | 12/1995 | European Pat. Off. . |
| WO 93/21824 | 11/1993 | WIPO . |

OTHER PUBLICATIONS

Jaeho Kim, Joe Bocek, Harley White, Bill Crone, Cliff Alferness, John Adams, "An Atrial Fibrillation Detection Algorithm for an Implantable Atrial Defibrillator," Computers in Cardiology 1995, Sep. 10–13, 1995, Vienna, Austria, The Institute of Electrical and Electronics Engineers, Inc.

Tim K. Peters, H.E. Koralewski and E. Zerbst, "The Principle of Electrical Carotid Sinus Nerve Stimulation: A Nerve Pacemaker System for Angina Pectoris and Hypertension Therapy", *Annals of Biomedical Engineering*, vol. 8, pp. 445–458, 1980.

Terry B. Cooper, Gilbert R. Hageman, Thomas N. James, and Albert L. Waldo, "Neural Effects on Sinus Rate and Atrioventricular Conduction Produced by Electrical Stimulation from a Transvenous Electrode Catheter in the Canine Right Pulmonary Artery" *Circulation Research*, vol. 46, No. 1, Jan. 1980.

Aydin M. Bilgutay, M.D., Ilhan M. Bilgutay, B.E.E., Frederick K. Merkel, M.D., and C. Walton Lillehei, Ph.D., M.D., "Vagal Tuning", *Journal of Thoracic and Cardiovascular Surgery*. vol. 56, No. 1, Jul. 1968.

P.E. Konrad, Ph.D., W.A. Tacker, Jr., M.D., Ph.D., J.D. Bourland, Ph.D., L.A. Geddes, Ph.D., and D. Hood, R.V.T., R.N., "A New Implantable Arterial Pulse Sensor for Detectio of Ventricular Fibrillation", *Medical Instrumentation*, vol. 22, No. 6, Dec., 1988.

Primary Examiner—William E. Kamm
Assistant Examiner—George R. Evanisko
Attorney, Agent, or Firm—Woodard, Emhardt, Naughton Moriarty & McNett

[57] ABSTRACT

A closed-loop variable frequency vagal stimulation apparatus for control of ventricular rate during atrial fibrillation. In one embodiment the apparatus includes a stimulator applied to the left vagus nerve and a proportional controller programmed to automatically and continuously adjust the vagal stimulation frequency proportionally as a function of the difference between actual and desired ventricular excitation rates. In a second embodiment the apparatus includes a vagal nerve stimulator and a controller which automatically adjusts the vagal stimulation frequency as a function of the difference between ventricular excitation rate and arterial pulse rate in order to eliminate or minimize pulse deficit.

5 Claims, 3 Drawing Sheets

U.S. PATENT DOCUMENTS

| | | |
|---|---|---|
| 5,154,172 | 10/1992 | Terry et al. . |
| 5,193,550 | 3/1993 | Duffin .................................. 128/705 |
| 5,199,428 | 4/1993 | Obel et al. ........................... 128/703 |
| 5,203,326 | 4/1993 | Collins ................................. 607/4 |
| 5,215,089 | 6/1993 | Baker . |
| 5,222,494 | 6/1993 | Baker . |
| 5,243,980 | 9/1993 | Mehrz ................................... 128/703 |
| 5,330,507 | 7/1994 | Schwartz .............................. 128/705 |
| 5,335,657 | 8/1994 | Terry et al. . |
| 5,480,413 | 1/1996 | Greenhut et al. . |
| 5,522,852 | 6/1996 | White et al. .......................... 607/5 |

METHOD AND APPARATUS USING VAGAL STIMULATION FOR CONTROL OF VENTRICULAR RATE DURING ATRIAL FIBRILLATION

BACKGROUND OF THE INVENTION

This invention relates to devices and methods for controlling ventricular rate during atrial fibrillation, and more particularly to such devices and methods employing nerve stimulation techniques.

Atrial tachycardia, flutter and fibrillation are serious arrhythmias resulting in a low cardiac output and limited exercise tolerance. At present these arrhythmias are treated with drugs, electric shock (cardioversion), or surgical destruction of the atrioventricular (A-V) node and pacemaker implantation. Drug therapy is not always effective and there are undesirable side effects. Although cardioversion abolishes some of these atrial arrhythmias, they usually return because the cause for the arrhythmia is still present. Surgical treatment is successful but leaves the subject with a limited exercise tolerance unless a rate-responsive pacemaker is implanted. These existing approaches are accepted by the medical community and biomedical engineers as the only practical choices, despite the existence of research reported in the literature for years on the subject of electrophysiological techniques involving stimulation of various nerves.

To understand the mechanism of action of an alternative system, proposed herein, for ventricular rate control by means of control of the number of atrial excitations reaching the ventricles, it is useful to review some aspects of the effect of cholinergic drive on the heart. Acetylcholine hyperpolarizes the S-A node and atrial muscle membranes, reduces the refractory period of atrial muscle and weakens the force of atrial contraction. Cholinergic drive also delays or blocks the transmission of excitation across the A-V node.

The cholinergic nerves to the heart are the right and left vagii. The right vagus innervates the S-A node, the atrial muscle and, to a much lesser degree, the A-V node. The left vagus nerve innervates the S-A node and atrial muscle to a lesser degree than it innervates the A-V node. It is well known to physiologists that stimulation of the right vagus nerve predominately slows the S-A node rate and thereby reduces heart rate. Stimulation of the left vagus nerve produces some slowing of the S-A node, prolongation of A-V conduction and partial or total A-V block. We have observed in monophasic atrial electrograms that low-frequency left vagal stimulation causes a dramatic shortening of the duration of the atrial monophasic action potential, indicating shortening of the refractory period. Although the left vagus nerve affects atrial rate to a lesser degree, transmission of excitation across the A-V node is largely regulated by the left vagus nerve.

In atrial fibrillation, the A-V node is bombarded with excitations and responds as rapidly as its refractory period will allow, resulting in rapid, irregular ventricular excitations, i.e., R waves, resulting in varying times for ventricular filling. This results in a rapid, irregular pulse with a pulse deficit. A pulse deficit exists when a ventricular excitation (R wave) does not produce a blood pressure pulse. The mean blood pressure and cardiac output are both reduced as a result of the pulse deficit.

There have been some reports of using electrodes to stimulate the vagus nerve, where such stimulation has an effect on heart rhythm. See, e.g., Bilgutay et al., Vagal Tuning, *J. Thoracic Cardiovas. Surg.* 56(1):71–82, July, 1968. Bilgutay et al. studied the use of vagal stimulation for treatment of supraventricular arrhythmias, angina pectoris, and heart failure. Experiments were conducted to determine the effective amplitudes, frequencies, wave shapes and pulse length of the stimulating current to achieve an optimal slowing of the heart rate by stimulating the vagus nerve, the optimal heart rate being defined as the slowest heart rate that could be attained by vagal stimulation without causing A-V dissociation or complete heart block or lowering the ventricular and aortic pressures. The experiments involved the right vagus nerve and resulted in selection of a stimulation amplitude of 6 to 10 volts, a frequency of 10 pulses per second, and 0.2 msec. pulse duration. Voltage increases were noted to decrease heart rate, and a unit triggered by the R waves of the subject's electrocardiogram is described as operating on a servo principle, but apparently in all cases the amplitude and frequency settings are fixed whenever the unit is operating. Bilgutay et al. indicated that the right vagus nerve was stimulated because its distribution is known to be mostly to the sinus node area, but mentioned one experiment in which stimulation of the left vagus slowed the ventricular beats in a dog with complete heart block.

Recognizing the possibility of bradyarrhythmia, one recently proposed approach contemplates the inclusion of cardiac pacing with vagal stimulation. This latter approach to heart rate control, which entails a bradyarrhythmia pacemaker, is described in PCT International Publication No. WO 93/21824, published Nov. 11, 1993. The addition of pacemaker circuitry and related components naturally increases the complexity and cost of the medical device. The publication mentions that stimulation frequency may be varied in a predetermined pattern from an optimum stimulation frequency, amplitude and duration determined during patient workup, if the initial delivered therapy fails to convert the tachyarrhythmia; however, there is no indication of a suitable pattern or any method of implementing it. The device described is designed to generate nerve stimulating pulses having a frequency and amplitude that, while programmable, are fixed once programmed. In essence it is an ON/OFF device that switches state in response to, e.g., the crossing of a heart rate threshold. Such ON/OFF switching, with fixed pulse characteristics, is likely to produce a hunting response, i.e., cycling of the heart rate with episodes of tachycardia.

Thus there remains the need for a system that effectively takes advantage of the phenomenon that transmission across the A-V node is largely, but not entirely, regulated by the left vagus nerve, and, more particularly, provides effective control of electrical stimulation of the vagus nerve to control the number of excitations that reach the ventricles during atrial fibrillation.

SUMMARY OF THE INVENTION

The present invention overcomes the foregoing and other disadvantages of the prior art by providing a closed-loop, variable frequency vagal stimulation apparatus for control of ventricular rate during atrial fibrillation. The apparatus includes a stimulating means for stimulating a vagal nerve at a stimulation frequency which is varied automatically in response to sensed conditions, and a controller having an output connected to said stimulating means and including means for automatically and continuously adjusting said vagal stimulation frequency as a function of the difference between actual and desired ventricular excitation rates.

According to another aspect of the present invention, there is provided an apparatus for automatically controlling ventricular rate by vagal stimulation to minimize pulse deficit during atrial fibrillation. The apparatus includes a stimulating means for stimulating a vagal nerve at a stimulation frequency which is varied automatically in response to sensed conditions, a means for detecting a ventricular excitation rate, a means for detecting an arterial pulse rate, and a processing means for comparing said ventricular excitation rate and said arterial pulse rate and automatically adjusting said vagal stimulation frequency as a function of the difference between said ventricular excitation rate and said arterial pulse rate.

A general object of the present invention is to provide an improved method and apparatus for controlling ventricular rate in the presence of atrial fibrillation.

A further object is to provide effective control of ventricular rate via vagal stimulation.

Another object of the invention is to provide an effective method and apparatus for stimulating the vagus nerve and thereby reducing ventricular rate enough to eliminate or minimize the pulse deficit which typically occurs during atrial fibrillation.

DETAILED DESCRIPTION OF THE PREFERRED EMBODIMENT

Figure 1:
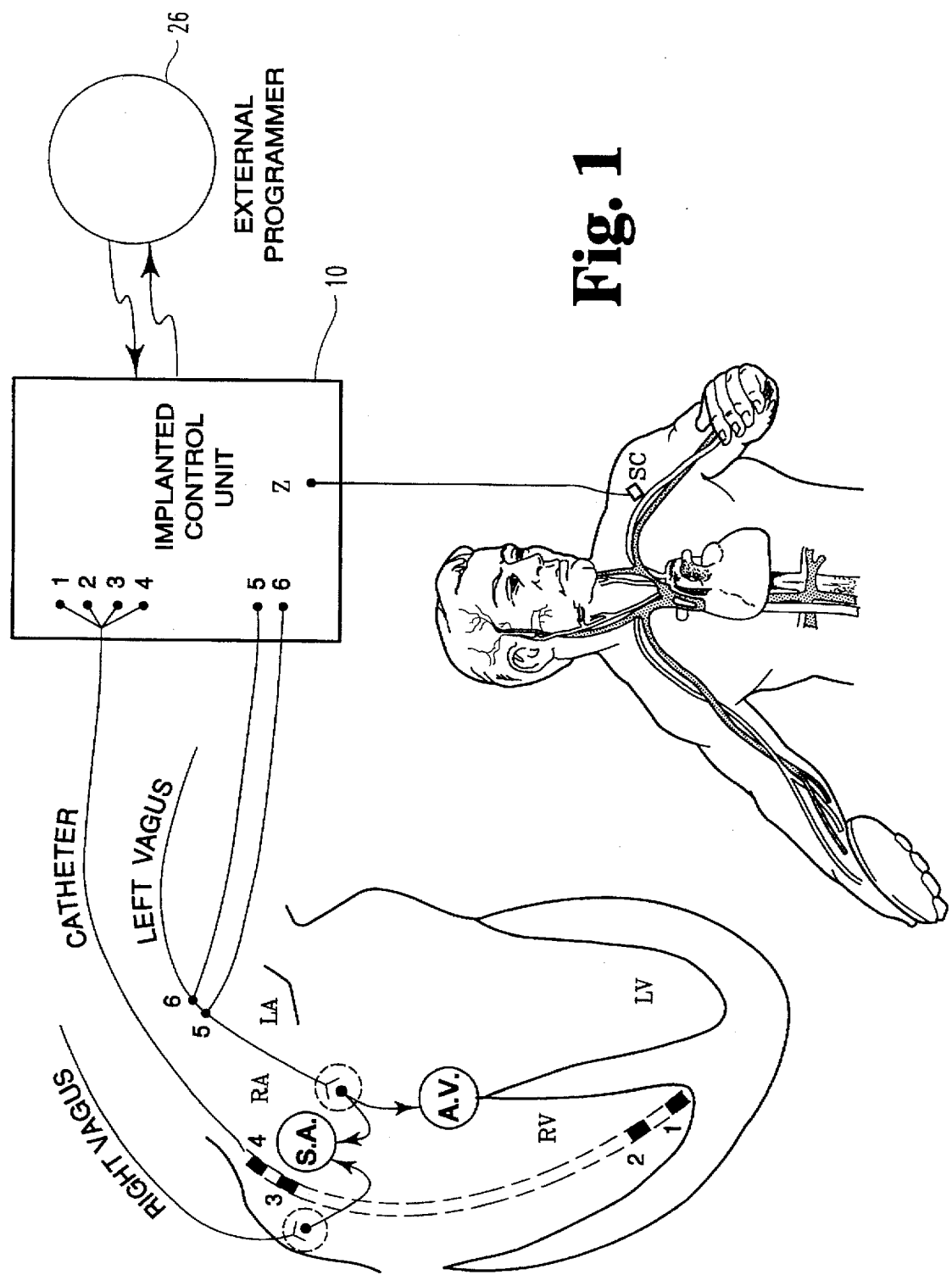
FIG. 1 is an illustration of an implanted control unit according to the present invention in its operating environment showing the heart and left and right vagus nerves.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

FIG. 1 illustrates an implantable device according to the present invention in its operating environment in a mammalian body, in which it is operatively connected to the heart and the left vagus nerve. Information on the electrical activity of the ventricles and the atria is obtained by a catheter having two pairs of electrodes: electrodes 1 and 2 in the right ventricle (RV) and electrodes 3 and 4 in the right atrium (RA). Electrodes 1 and 2 are designed and positioned to detect a ventricular electrogram, which is supplied to the implanted controller unit 10 which processes the ventricular electrogram and derives therefrom the ventricular excitation rate. Electrodes 3 and 4 are designed and positioned to detect an atrial electrogram, which is supplied via the catheter to the implanted control unit, which processes the atrial electrogram. The implanted control unit includes logic circuitry or other circuit means for comparing the atrial and ventricular signals in terms of synchronization and rate, and on the basis of that comparison determining whether or not the patient is experiencing atrial fibrillation. The implantable device includes a pair of electrodes 5 and 6 attached or adjacent to the left vagus nerve for controlled stimulation thereof. One embodiment of the present invention, described below, also includes a sensor of instantaneous blood pressure, in the form of a monopolar impedance-measuring electrode applied to the surface of the subclavian (SC) artery. Alternately, a piezoelectric pulse pickup placed alongside an artery could be used. A piezoelectric device would generate a voltage pulse and therefore save battery life in an implanted control unit dependent on a battery for operation.

The two embodiments of the invention to be described below are desirably combined in a single implanted control unit operable in two modes respectively associated with the control algorithms for the first and second embodiments. Both embodiments use an adaptive control system which adjusts to changing cardiac states. It operates only during episodes of atrial fibrillation. It retains, in memory, parameters that were successful in previous episodes of required control and uses this previously learned information to improve controller responses under similar situations. It also uses this information to accelerate controller adjustments in newly encountered situations.

The first embodiment and its associated algorithm will be described in connection with FIG. 2, which depicts in block diagram form, a controller 20 as an important aspect of the implanted control unit. The ventricular and atrial signals are supplied from their respective electrodes in the heart to a ventricular electrogram detector 22 and atrial electrogram detector 24, respectively, which digitize the electrograms and supply the digitized signals to controller 20, which responds to the detected ventricular and atrial signals. More specifically, atrial rate is determined on the basis of the interval between atrial waves and is compared to a threshold established as an indication of atrial fibrillation. If desired, the time interval itself may be measured and compared to a time interval threshold for the same purpose. Other techniques and algorithms for detection of atrial fibrillation with a lead configuration of multiple catheters including one in the right atrium and another in the coronary sinus are disclosed in an article by Kim et al. entitled "An Atrial Fibrillation Detection Algorithm for an Implantable Atrial Defibrillator", *Computers in Cardiology*, 1995, IEEE 1995: 169–172, which article is hereby incorporated by reference.

Figure 4:
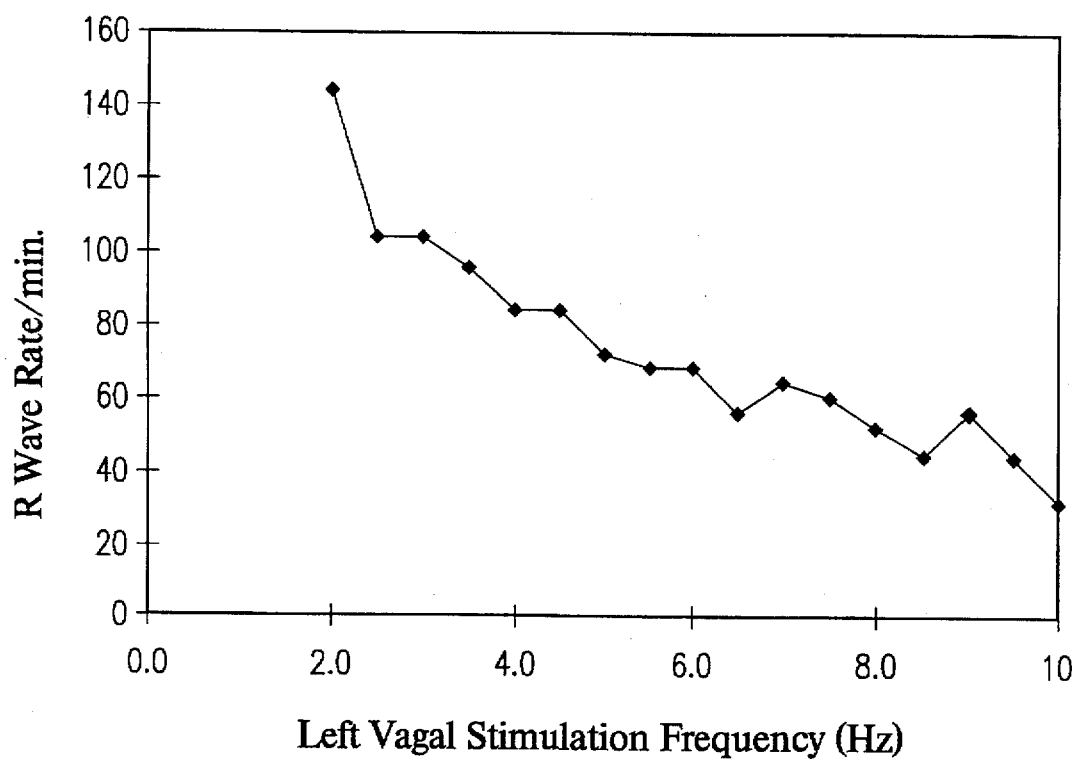
FIG. 4 is a graphical illustration of the relationship between ventricular rate and left vagal stimulation frequency.

In the presence of atrial fibrillation, the controller is enabled to compare the actual R-wave rate with a target rate 25 entered into the controller via an external programmer 26 (FIG. 1) and, based on the difference between those rates, to control the frequency of the pulses which are generated by a stimulator 28 connected via electrodes 5 and 6 to the left vagus nerve. The controller is preferably programmed to apply a low initial frequency, and consequently, to increase the stimulus frequency slowly and incrementally until the ventricular rate matches the operator-selected target rate, and to automatically and continuously adjust the vagal stimulation frequency as a function of the difference between the actual and desired ventricular excitation rates. FIG. 4 illustrates the smooth control of ventricular rate that can be exerted by vagal stimulation during atrial fibrillation. A steady increase in stimulation frequency enabled the ventricular rate to be decreased smoothly, in an almost linear manner, down to a rate of 35 bpm with a stimulation frequency of 10 pulses/second. A pulse width of 100 microseconds (μsec.) has been found suitable, and pulse widths up to 2 msec. may also be effective in some applications. The pulse width is preferably in the range of 100–200 μsec. for A and B fibers, and in the range of 500–750 μsec. for C fibers. A suitable implantable stimulator is described in detail in U.S. Pat. No. 5,154,172, which is hereby incorporated by reference.

Figure 3:
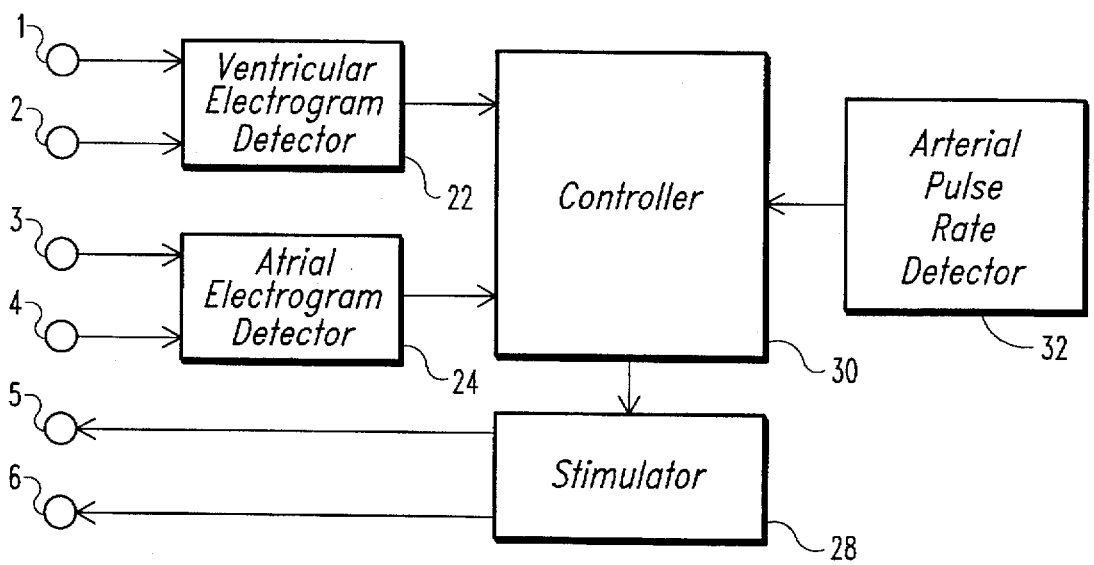
FIG. 3 is a block diagram of another form of the implanted control unit of FIG. 1.
Figure 5:
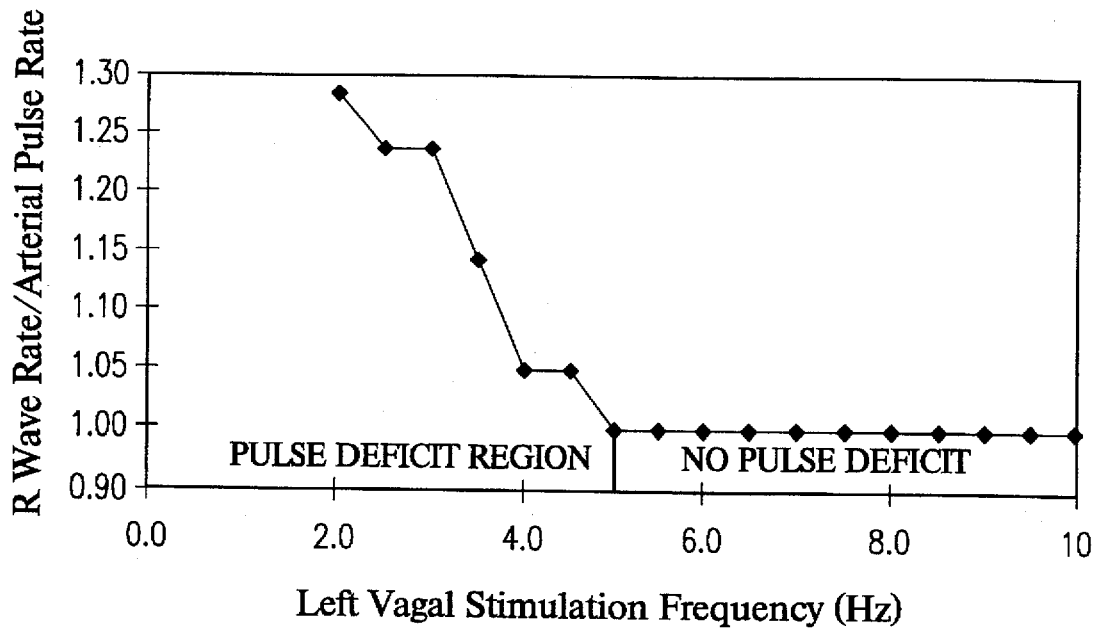
FIG. 5 is a graphical illustration of the ratio of R wave rate to arterial pulse rate versus the frequency of left vagal stimulation.

Referring to FIG. 3, the second embodiment or mode of the present invention operates according to an algorithm designed for elimination of a pulse deficit, i.e., the condition in which an arterial pulse fails to occur in response to an R wave. This algorithm does not require the selection of a target ventricular rate and is therefore operator-independent. The objective of this closed-loop control method is to identify the lowest stimulus frequency required be applied to the left vagus nerve to achieve a ventricular rate with no pulse deficit. As will be described, the controller 30 is designed and programmed to monitor the blood pressure signal for an arterial pulse after every ventricular excitation (as indicated by the R wave of the ECG), and, in general terms, to use the pulse deficit to control the frequency of stimuli applied to the left vagus nerve in order to identify the minimum stimulus frequency for which each ventricular excitation produces a blood pressure pulse. The controller is programmed to implement an algorithm corresponding generally to the graph illustrated in FIG. 5, although it will be understood that the shape and values of such a graph will vary somewhat for individual patients and that the automatic control algorithm will be varied accordingly. The ventricular and atrial electrogram detectors 22 and 24 digitize the electrogram signals and supply them to the controller, which also receives digitized data from an arterial pulse detector 32, described in further detail below.

There are several important considerations in achieving closed-loop control to eliminate the pulse deficit in atrial fibrillation. The first is recognition that inhibition of impulses traveling from the atria to the ventricles using vagus stimulation is not instantaneous. From the initiation of a train of stimuli applied to the vagus nerve, the onset of slowing of the ventricular (R wave) rate depends somewhat on the frequency of the stimuli in the train; the higher the frequency, the sooner the onset of ventricular slowing.

Another important consideration is adoption of an amplitude criterion for pulse counting. During atrial fibrillation, the arterial pulses vary widely in amplitude. However, a pulse should occur in a time window just after the R wave of the ECG, and so the R wave is preferably used to open a time window to measure the peak-to-peak amplitude of the arterial pulse in the window, which is sufficiently long to accommodate the isovolumic period and the pulse transit time to the arterial measuring site. In a typical situation the former is on the order of 150 msec. and with a measuring site close to the left ventricle, the latter may amount to 50–100 msec. A running average of the pulse amplitude is made, and each newly measured pulse is compared in amplitude to the mean pulse amplitude. Pulses less than a predetermined percentage (20% is presently preferred) of the mean pulse amplitude are treated as absent.

The amount of pulse deficit, is identified by the relationship between R waves and arterial pulse waves over a predetermined interval of time, for example, one minute. The controller's response to a pulse deficit is to apply low-frequency stimuli, e.g., initially 1 pulse per second, via stimulator 28. Controller 30 then counts and displays the ratio of R waves to arterial pulses. After 1 minute, if the pulse deficit has not been reduced, the controller increases the frequency of the stimuli applied to the vagus nerve to 2 pulses per second and evaluates the pulse deficit over the next one-minute period. This procedure of evaluating pulse deficit and incrementally increasing stimulus frequency continues until the pulse deficit disappears, or until a low R-wave rate safety limit is reached, at which point the controller maintains the current stimulus frequency.

An arterial pulse detector 32 for measuring arterial pulse rate and suitable for use with the present invention includes a monopolar arterial electrode made from a Teflon-coated stainless steel wire, insulated except at its distal end, which is sutured to a small sheet of Dacron-reinforced Silastic. The Dacron sheet carrying the electrode is wrapped around the subclavian artery as shown in FIG. 1, or other convenient artery, and sutured. The monopolar arterial electrode operates in conjunction with a reference electrode which is relatively large and located at any convenient site, for example, the metal case of the implanted control unit. Further details of an arterial pulse detector as described above are described in an article by Konrad et al. entitled "A New Implantable Arterial Pulse Sensor for Detection of Ventricular Fibrillation," *Medical Instrumentation* 22(6):304–311, December, 1988, which article is hereby incorporated by reference. Alternatively, and especially for experimental studies, the arterial pulse may be measured directly, e.g., with a piezoelectric pulse pickup as indicated above.

A suitable electrode presently preferred for attachment to the vagus nerves is a helical cuff electrode described in detail in U.S. Pat. Nos. 4,573,481 and 5,154,172, which are hereby incorporated by reference.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, those skilled in the art will appreciate from the foregoing teachings of the present invention that other embodiments can be used to implement the principle of ventricular rate control during atrial fibrillation using controlled vagal stimulation. For example, both vagus nerves may be stimulated to obtain more A-V block. Alternately, only the cardiac branches of the vagus nerves (left and/or right) may be stimulated to minimize any possible gastrointestinal effects.

Figure 2:
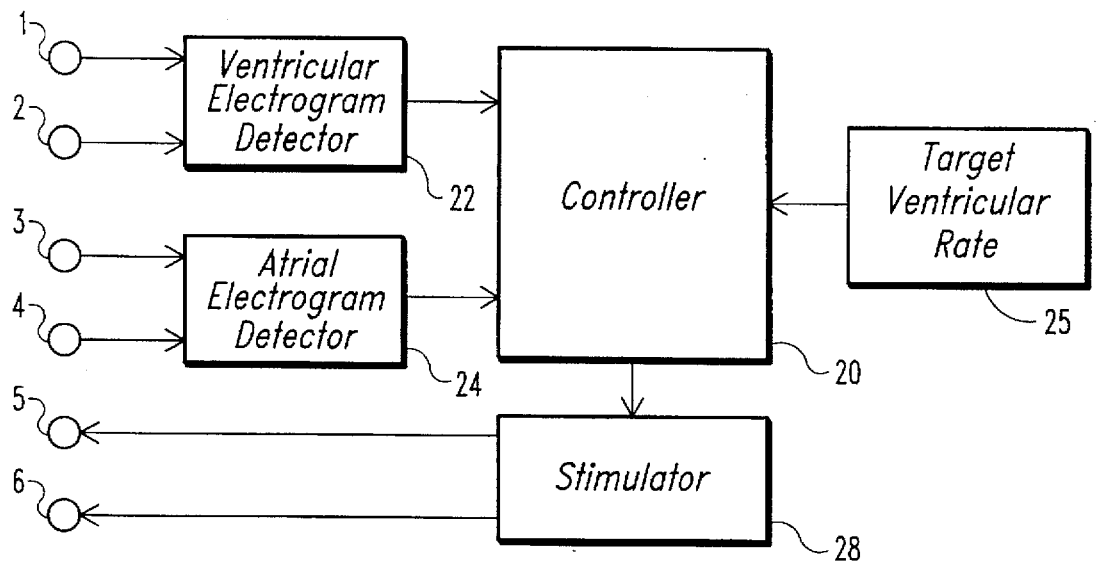
FIG. 2 is a block diagram of one form of the implanted control unit of FIG. 1.

The embodiments illustrated in FIGS. 1 and 2 employ a catheter electrode in the right atrium and ventricle and another electrode on the left vagus nerve. An alternate embodiment could use a catheter electrode in the right pulmonary artery to stimulate the left vagus nerve, as described by Cooper et al. (Circ. Res. 1980, 46:48–57). In this way, the principle can be applied using catheter electrodes.

Another embodiment avoids blood contact by using electrodes applied to the pericardium to detect the atrial and ventricular electrograms.

We claim:

1. An apparatus for automatically controlling ventricular rate by vagal stimulation to minimize pulse deficit during atrial fibrillation, comprising:

stimulating means for stimulating a vagal nerve at a variable stimulation frequency;

means for detecting a ventricular excitation rate;

means for detecting an arterial pulse rate;

processing means for comparing said ventricular excitation rate and said arterial pulse rate and automatically adjusting said vagal stimulation frequency as a function of the difference between said ventricular excitation rate and said arterial pulse rate.

2. The apparatus of claim 1, wherein said processing means includes means for adjusting the vagal stimulation frequency as a function of the ratio of said ventricular excitation rate to said arterial pulse rate.

3. The apparatus of claim 2, wherein said processing means increases said vagal stimulation frequency at predetermined intervals until said pulse deficit is substantially eliminated.

4. The apparatus of claim 3, further comprising means for enabling generation of stimulating pulses only in the presence of atrial fibrillation.

5. The apparatus of claim 3, in which the predetermined interval is in the range of approximately one to ten minutes.

* * * * *